(12) United States Patent
Kramer

(10) Patent No.: US 10,799,184 B2
(45) Date of Patent: Oct. 13, 2020

(54) SYSTEM AND METHOD FOR THE IDENTIFICATION AND SUBSEQUENT ALERTING OF HIGH-RISK CRITICALLY ILL PATIENTS

(71) Applicant: Prescient Healthcare Consulting, LLC, Charlottesville, VA (US)

(72) Inventor: Andrew Alan Kramer, Charlottesville, VA (US)

(73) Assignee: Prescient Healthcare Consulting, LLC, Charlottesville, VA (US)

( * ) Notice: Subject to any disclaimer, the term of this patent is extended or adjusted under 35 U.S.C. 154(b) by 265 days.

(21) Appl. No.: 15/921,723

(22) Filed: Mar. 15, 2018

(65) Prior Publication Data

US 2018/0271454 A1    Sep. 27, 2018

Related U.S. Application Data

(60) Provisional application No. 62/477,048, filed on Mar. 27, 2017.

(51) Int. Cl.
*A61B 5/00* (2006.01)
*A61B 5/0205* (2006.01)
(Continued)

(52) U.S. Cl.
CPC ........ *A61B 5/7275* (2013.01); *A61B 5/02055* (2013.01); *A61B 5/14532* (2013.01); *A61B 5/14542* (2013.01); *A61B 5/14546* (2013.01); *A61B 5/743* (2013.01); *A61B 5/7405* (2013.01); *G16H 10/60* (2018.01); *G16H 50/30* (2018.01);
(Continued)

(58) Field of Classification Search
CPC .... G16H 10/00–80/00; G06Q 10/00–2250/00; G06F 1/00–2221/00
See application file for complete search history.

(56) References Cited

U.S. PATENT DOCUMENTS 9,679,341 B2 *   6/2017   Kocis et al. ........... G06Q 50/22
2014/0350369 A1 *  11/2014  Budinnan et al. ............ 600/365
(Continued)

FOREIGN PATENT DOCUMENTS

WO    WO-2011/115576 A2 *  9/2011

OTHER PUBLICATIONS

"Vocera communication badge", Retrieved from Internet: https://web.archive.org/web/20160420232543/http://www.vocera.com/product/vocera-communication-badge (Year: 2016).*
(Continued)

*Primary Examiner* — Elaine Gort
*Assistant Examiner* — Menglu Wu
(74) *Attorney, Agent, or Firm* — John H. Thomas, P.C.

(57) ABSTRACT

The system and method described herein represent a totally new paradigm for assessing risk in critically ill patients by identifying physiologic patterns associated with a poor outcome. It then uses this information to detect these patterns on future patients, sending alerts to clinicians caring for patients with one or more of them. Moreover, the system and method can be extended to outcomes other than mortality, and can be adapted for use in a specific hospital system's EMR. The "code footprint" for embedding the patterns that indicate a trigger is small and thus favorably suited for embedding into an existing clinical decision support system.

7 Claims, 11 Drawing Sheets

(51) Int. Cl.
*A61B 5/145* (2006.01)
*G16H 10/60* (2018.01)
*G16H 50/30* (2018.01)
*A61B 5/021* (2006.01)
*A61B 5/024* (2006.01)
*A61B 5/08* (2006.01)

(52) U.S. Cl.
CPC ............... *A61B 5/021* (2013.01); *A61B 5/024* (2013.01); *A61B 5/0816* (2013.01)

(56) References Cited

U.S. PATENT DOCUMENTS

2017/0249445 A1* 8/2017 Devries et al.
2017/0262597 A1* 9/2017 Huddar et al. .......... G06F 10/00

OTHER PUBLICATIONS

YouTube video clip entitled "Vocera Patient Monitoring integration" Retrieved from Internet: https://www.youtube.com/watch?v=ZHnw8Xy3rm0 (Year: 2012).*

* cited by examiner

SYSTEM AND METHOD FOR THE IDENTIFICATION AND SUBSEQUENT ALERTING OF HIGH-RISK CRITICALLY ILL PATIENTS

This application claims the benefit of U.S. Provisional Patent Application No. 62/477,048, filed Mar. 27, 2017, which is incorporated herein by reference in its entirety.

The present invention is a system and method originally designed for use in an intensive care unit in a health care provider facility. The method and system, using patient physiological information, can alert a care-provider that there is a patient at high risk for a deleterious outcome based on the comparison of individual patient information to trends identified as deleterious in a database of historical patient information.

BACKGROUND

The intensive care unit (ICU) in an acute care hospital is a data rich environment. Almost all patients are hooked up to a bedside monitor, yielding high-frequency physiologic measurements. However patients in an ICU have a high risk of deleterious outcomes, most notable deterioration and/or mortality. While some at-risk patients are easily identified, others seem to be stabilized but then almost suddenly go into decline.

Prior attempts to generate alerts in the ICU have been of limited utility because of at least one or more of the following reasons: 1) a method included only one physiologic measure, e.g. heart rate; 2) traditional linear time series approaches were used to analyze data; 3) patterns of variability based on maximum entropy or fractal dimension were used (which have not proven to be highly predictive of patient deterioration); and 4) indication of an at-risk patient was not sent to clinicians, but rather appeared on a unit's screen consisting of all patients.

In one prior system, a severity of illness measure utilizes physiologic values and cut-points to predict mortality in critically ill patients. This system only looks at a patient's first day in the ICU, and for each physiologic measure, takes the single value that is the furthest from what is considered normal. It is also used only retrospectively to benchmark ICUs, and does not look for patterns over time for a physiologic measurement. Finally, it has no means of generating a patient alert. It is only used to measure observed vs predicted outcomes in aggregate across ICUs.

Other predictive models have similar drawbacks. Two processes for looking at sequential physiologic measurements have been reported. The first process uses a recurrent neural network to provide predictions, which is extremely difficult to embed into a new client's EMR workflow. It has no alerting mechanism and is subjective as to which prediction threshold should be denoted as "high risk". The second process is an attempt to generate scores throughout a patient's stay by continually searching for the worst vital signs values instead of including all values to look at patterns. According to the methodology a prediction is feasible only after 12 hours has elapsed, rendering it useless for early detection of possible patient deterioration.

A prior attempt uses words to denote patterns in a quantitative variable. It uses an unsupervised method (i.e. no outcome) to look for sequences within a single unit of observation over time (e.g. stock price, quarterly sales, etc. . . . ). It does not attempt to associate words with outcomes across a population in order to generate risk categories for future patients. Second, it standardizes all values to a normal distribution for a single vital sign, and then determines cut-points based on quantiles. Finally, the order of letters is important in this prior system. A measurement mapped to the letter "A" is necessarily higher than a measurement mapped to the letter "B", which is greater than a measurement mapped to the letter=C, etc. . . . .

SUMMARY

This invention solves the foregoing problems and provides a novel multi-step system and process that inputs streaming vital signs data, identifies patterns in that data that are associated with a high risk of an adverse outcome, and then sends alerts to clinicians caring for those patients. By utilizing the system and method, it might be possible for clinicians to detect patients with a high risk of an adverse outcome in a timely fashion, enabling effective remedial treatment. The system is comprised of two parts. The first part analyzes physiologic data from a hospital's EMR system and discovers data patterns that presage a deleterious outcome. These data patterns are stored in a first database. Once these patterns have been revealed, the second part of the system embeds the detection of these patterns into a hospital's EMR, for the purpose of generating alerts when a new patient has one of these patterns. The alert, in one example a color-coded signal, is then sent to a mobile device or tablet of the clinicians caring for the patient.

The system and process described herein can identify patients at a high risk for deterioration long before the patient is clinically symptomatic. The ability to identify these patients early in their ICU stay may permit interventions that can reverse a patient's course. Further, this system and method stratifies patients into risk categories, resulting in a color-coded alert sent to clinical staff caring for that patient. The color codes indicate the level of risk for that patient. The present methodology can be extended for use at other time points during a hospitalization for alerting other clinical outcomes: need for a specific clinical intervention (e.g. patient requires mechanical ventilation), readmission to the ICU, mortality in the hospital unit after a patient has been discharged from the ICU.

The system and process include seven steps that generate computer code for completing the following tasks within a hospital system's ICUs:

1. Collect streaming physiologic data from an electronic medical record (EMR) system for patients admitted to an ICU, and segments each into bins that maximize the variation in mortality.
2. Create a mapping of patient data over consecutive time periods of the aforementioned bins into a symbolic representation ("letters").
3. Concatenate letters over consecutive time periods to form "words".
4. Ascertain which words are associated with increasing the risk of mortality.
5. Generate computer code for identifying the high-risk words.
6. Embed this code into a hospital's EMR system for application to future patients.
7. Based on the number of high-risk words, send alerts to clinicians caring for adult patients in an intensive care unit via a cell phone or other mobile device. The alerts indicate that a patient is at a significantly higher risk of an adverse clinical outcome, e.g. mortality.

The following list of definitions will be used throughout the remainder of this document.

Definitions

Physiologic measure: Any vital sign or lab measurement that gives information on a patient's medical condition. This may include, but is not limited to heart rate, respiratory rate, mean arterial pressure, $SaO_2$, temperature, glucose level, and platelet count.

Data point: A value for one physiologic measure at one point in time for a single patient. For example, a respiratory rate for John Doe taken on Mar. 3, 2017 at 1:00 am, a platelet count for Jim Smith taken on Mar. 3, 2017 at 6:35 am, a temperature for Sally Smith taken on Feb. 25, 2015 at 3:00 pm, etc. . . . .

Outcome: A clinical endpoint such as mortality, length of stay, readmission, etc. . . . . The death of a patient (mortality) is assumed to be a negative outcome.

Time Period: The duration of time over which physiologic measures are used to form a word (see below). For example, if a patient is hospitalized for 3 days & four hours, and the time period is two hours, then that patient would have 38 words generated over the course of their hospitalization.

Time Segment: The duration of time over which physiologic measures are used to form a let (see below). For example, if a time period is two hours and four letters comprise a word, then the time segment is 30 minutes.

Personal Median: The median value of all data points for a physiologic measure for a single individual during a specific time segment. For example, John Doe's median heart rate over the first 30 minutes after admission, if a time segment is 30 minutes long.

Cut-points: Specific values within the overall range for a physiologic measurement that divide up the distribution into bins. For example, if heart rate ranges from 5 bpm to 140 bpm, and the cut-points are 30, 52, 75 and 100, then a heart rate value can be mapped to one of the following bins: minimum-30, 31-52, 53-75, 76-100 and 101-maximum. The bins are what define "letters" (see below). Cut-points emanate from maximizing the mortality rates across bins ("Maximum Mortality Variability", see below).

Maximum Mortality Variability (MMV): For a physiologic measure, the distribution of bins that result in the maximum variability in mortality rate. This is derived from using a genetic algorithm or other optimization method to select the cut-points that maximize the pairwise difference in mortality rates between bins (differences expressed as absolute values). Mathematically this is represented by optimizing the following function:

$$\frac{\sum_{i=1}^{n-1} \sum_{j=i+1}^{n} \text{abs}(m_i - m_j)}{\binom{n}{2}}$$

Where n=number of bins, $m_i$ is the mortality rate in bin "i", and $m_j$ is the mortality rate in bin "j".

For example, suppose respiratory rates ranged from 8-60, and two sets of cut-points yielded the following bins as shown in Table 1:

TABLE 1

Mortality rates for two hypothetical bins for respiratory rate

| Bins #1 | Mortality Rates #1 | Bins #2 | Mortality Rates #2 |
|---|---|---|---|
| 8-16 | .12 | 8-19 | .10 |
| 17-20 | .10 | 20-24 | .13 |
| 21-26 | .14 | 25-60 | .16 |
| 31-60 | .16 | | |
| Mortality Variability | (.02 + .02 + .04 + .04 + .06 + .02)/6 | | (.03 + .06 + .03)/3 |
| | .0367 | | .040 |

The mortality variability for Bins #1 is 0.0367 while the mortality variability for Bins #2 is 0.40. So Bins #2 has a higher mortality variability than Bins #1. The MMV is the set of cut-points that yield the highest mortality variability. Note that the number of cut-points is not fixed at a specific number.

Letter: A letter is assigned based on the personal median of a physiologic measure for a pre-determined time segment. For example, if a time segment is 30 minutes, there would be a letter assigned every 30 minutes. The assignment of letters is based on which bin a patient's personal median falls within for a specific physiologic measure. Consequently the number of letters is determined by the number of cut-points: the former is always one greater than the latter. An example is shown in Table 2. Suppose heart rate had the following cut-points: 32, 50, 76 and 105. This would yield bins of minimum-32, 33-50, 51-76, 77-105, and 106-maximum. A personal median heart rate of 28 would get assigned a letter of "A", a personal median heart rate of 49 would get assigned a letter of "B", etc. . . . . The assigned order of letters is not important and does not convey any information. In fact, letters could be any symbol, e.g. "%", "#", etc. . . . . The key point is that a letter/symbol denotes a specific range of physiologic values.

TABLE 2

Hypothetical assignment of letters to bins of median heart rates

| Cut-point | Resulting Bin | Letter |
|---|---|---|
| 32 | minimum-32 | A |
| 50 | 33-50 | B |
| 76 | 51-76 | C |
| 105 | 77-105 | D |
| | 106-maximum | E |

Word: A combination of letters formed over a specified time period. If the time period includes all data points collected over the course of two hours, and letters are formed every 30 minutes, then a word would consist of four letters. The next two hours would generate another word.

Trigger: A word that significantly increases the chance of an outcome, e.g. mortality.

Alert: Signal sent to clinicians' mobile phones or tablets when one of their patients has at least one trigger. In one example, the graphic for an alert is color coded based on the number of triggers.

In one example, a method for identifying and managing high-risk patients comprises the steps of providing a clinical setting for a first patient wherein the setting includes a plurality of physiological monitors and providing electronic devices to a caregiver in the clinical setting. The steps also include providing a first database that stores historical measurements of a plurality of former patient physiological measurements and former patient outcomes of those former patients, and defining trigger measurements based on the historical physiological measurements, wherein those trigger measurements represent a set of historical physiological measurements that have been identified as indicating a high risk for a negative clinical outcome. A second database is provided that receives and stores a plurality of measurements from the plurality of the first patient physiological monitors. Finally, the method includes comparing the first patient physiological measurements to the first database of historical measurements to identify a high-risk patient based on whether the first patient set of physiological measurements correspond to the first database trigger measurements; and sending an alert to the caregiver if the first patient is at a high risk for a negative outcome based on the comparing step. The method may include wherein the physiological measurements are selected from the group consisting of heart rate, respiratory rate, mean arterial pressure, saturated oxygen, temperature, glucose level, platelet count and white blood cell count. The physiological measurements may be recorded and saved for each of a predetermined time segment. For each historical physiological measurement, the steps may include dividing up the physiological measurements into ranges to form bins, wherein the distribution of bins results in the maximum variability in the historical mortality outcome rate. Each bin may be assigned a different letter. The first set of patient physiological measurements occur at a predetermined time segment, including alternatively, wherein each time segment is from about 5 to 30 minutes. Each bin may be assigned a different letter, and wherein a letter is assigned for each time segment for each physiological measurement depending on which bin the physiological measurement is in. The letters may be assigned for each physiological measurement and saved, and the letters are collected for a predetermined time period which is comprised of a plurality of time segments, wherein the plurality of letters associated with each time period form a word, and further wherein the trigger is a word that indicates an increase in the chance of a negative patient outcome. The word may have four letters. The alert sent to the caregiver comprises visual indicia sent to a user interface on the caregiver electronic device with respect to the specific patient or may comprise a visual and audible sound sent to the caregiver electronic device with respect to the specific patient.

BRIEF DESCRIPTION OF THE DRAWINGS

FIG. 6 is a hypothetical matrix of letters, words and triggers.

FIG. 7 a hypothetical demonstration of a patient receiving a score based on the number of triggers and outcome, which is summed.

DETAILED DESCRIPTION

The following research study will be used to illustrate how the present system and method are generated, and is referred to as the "STUDY". Of course other databases and information could alternatively be used and are expected to be used in a similar manner as described here.

Thirteen hospitals submitted data to a commercial centralized database ("Phoenix", Medical Decision Network, Charlottesville, Va.) for admissions to 29 intensive care units (ICU) during the timeframe of January 2012 through October 2017. This comprised 52,311 admissions. Data were obtained on each patient for heart rate, respiratory rate, mean arterial pressure, as well as mortality before discharge from the ICU. The 36,003 admissions from 2012 through 2015 were used to identify significant word patterns (i.e., the development data set), while the 16,308 admissions from the rest of the years were used to validate those results.

It was decided a priori that the first four hours after admission to the ICU were clinically important, and that a word would be generated every two hours, resulting in two words per physiologic measure per patient. As a result each word would contain four letters, letters corresponding to the personal median value for a physiologic measure every 30 minutes. The objective was to identify influential words that significantly increased the probability of a patient dying in the ICU at any time after four hours post-admission and before discharge from the ICU, and then enabling signals for those patients to be sent to mobile devices for the attending clinical staff.

Figure 1:
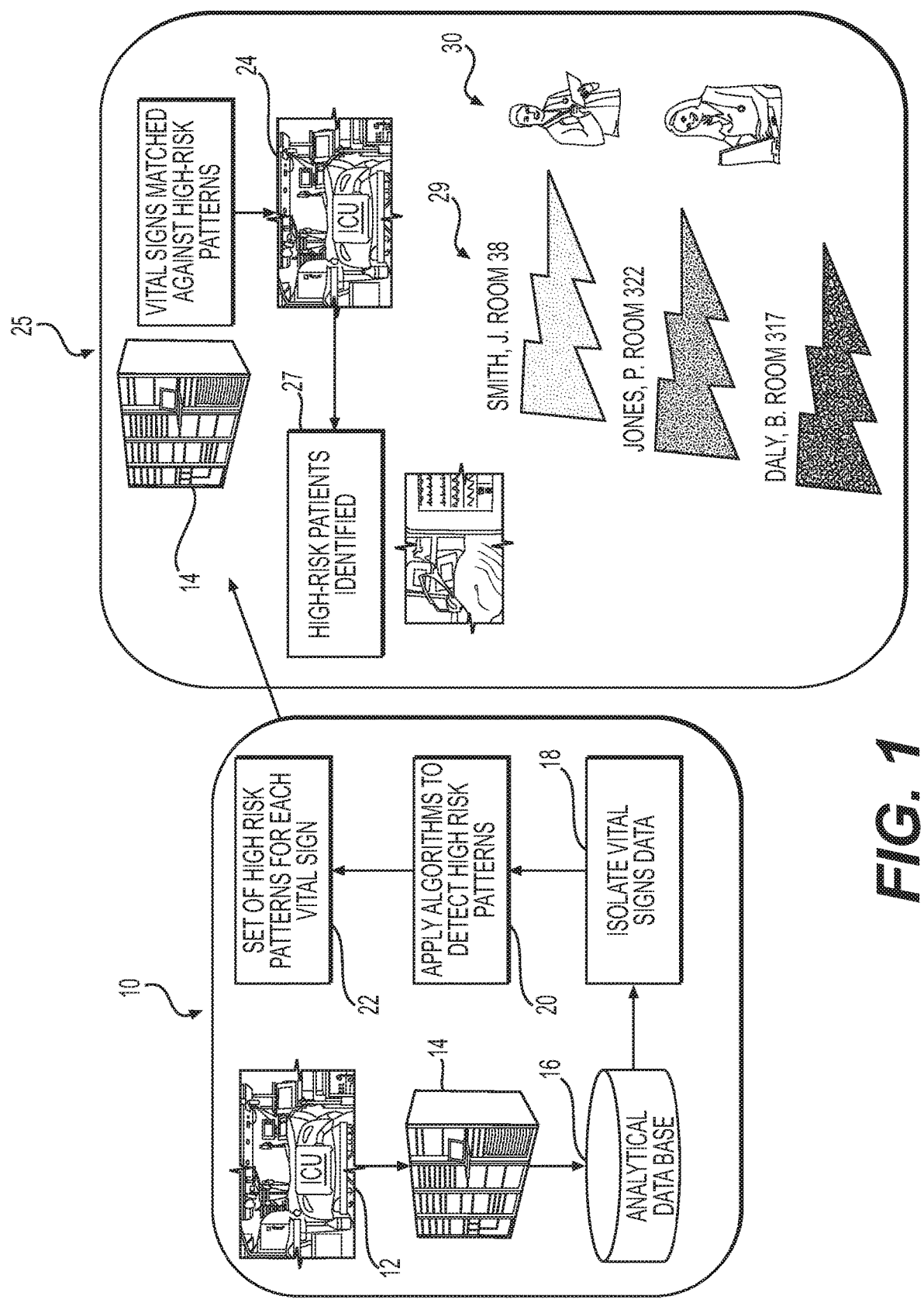
FIG. 1 is a schematic overview of the system and method described herein.

FIG. 1 is a schematic overview of the system and methods described herein. A historical database system 10 begins with a hospital ICU 12 that includes multiple physiological monitors, and the patient information from those monitors is stored in the hospital EMR system 14. Using an analytical database 16, a plurality of physiological vital signs data is collected 18. Algorithms are applied to the vital signs database 18 to detect high risk patterns 20 in those vital signs. Ultimately, a set of high risk patterns 22 is collected for each physiological vital sign. These high risk patterns 22 are then stored in the hospital EMR system 14. Using these high risk patterns 22, the EMR system 14 compares the physiological vital signs 24 of a new ICU patient in order to identify high risk patients 27. The identity of these high risk patients 27 is then sent to caregivers 30 by way of alerts 29. The process is described in more detail in the following.

Step One: Determination of the Cut-Points

Figure 2:
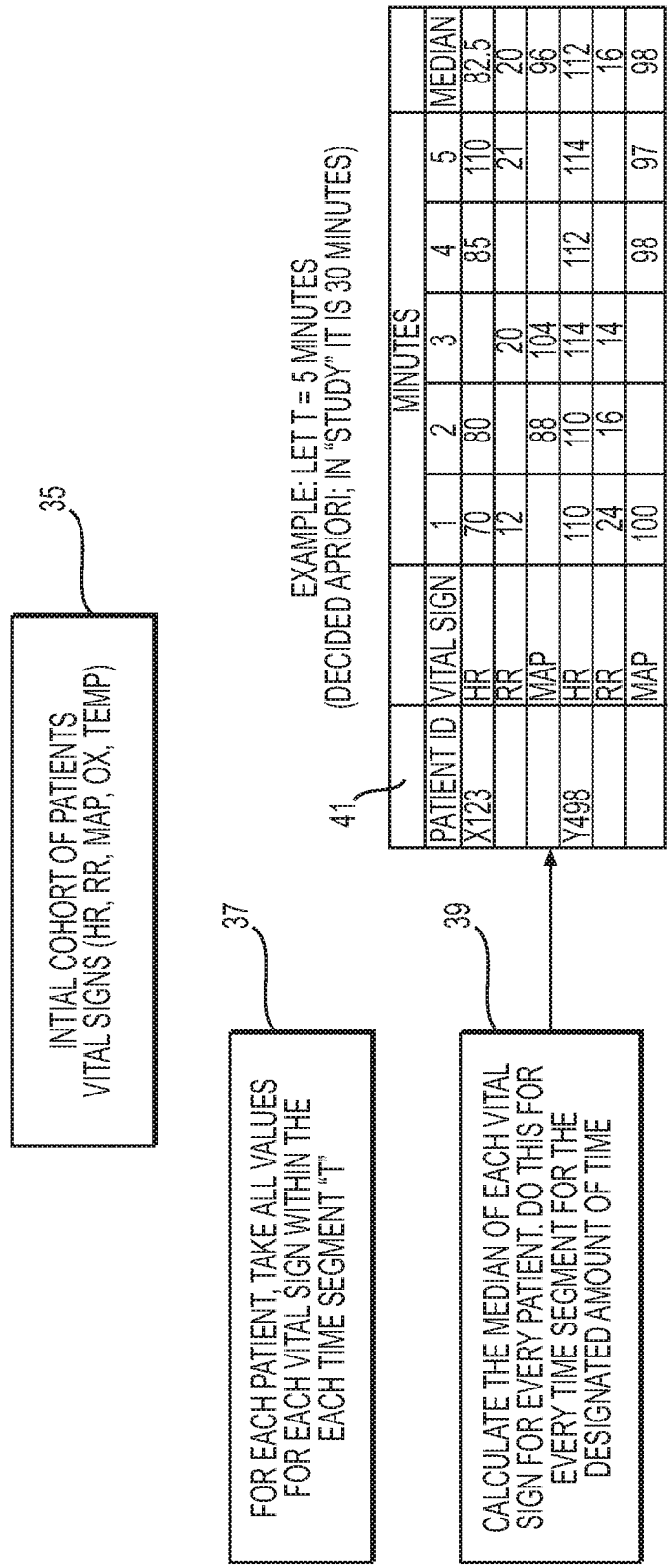
FIG. 2 is a demonstration of obtaining the median value of each physiological vital sign for every patient.

Initially, all historical patients have the median of each vital sign calculated across each time segment (FIG. 2). These historical patients are an initial cohort of patients 35 including all of their physiological vital signs. For each of these patients, all of the vital signs within each time segment are collected 37. The median of each vital sign for each patient and for each time segment is then calculated. A general example of a median table 41 for two patients is shown in FIG. 2.

Figure 3:
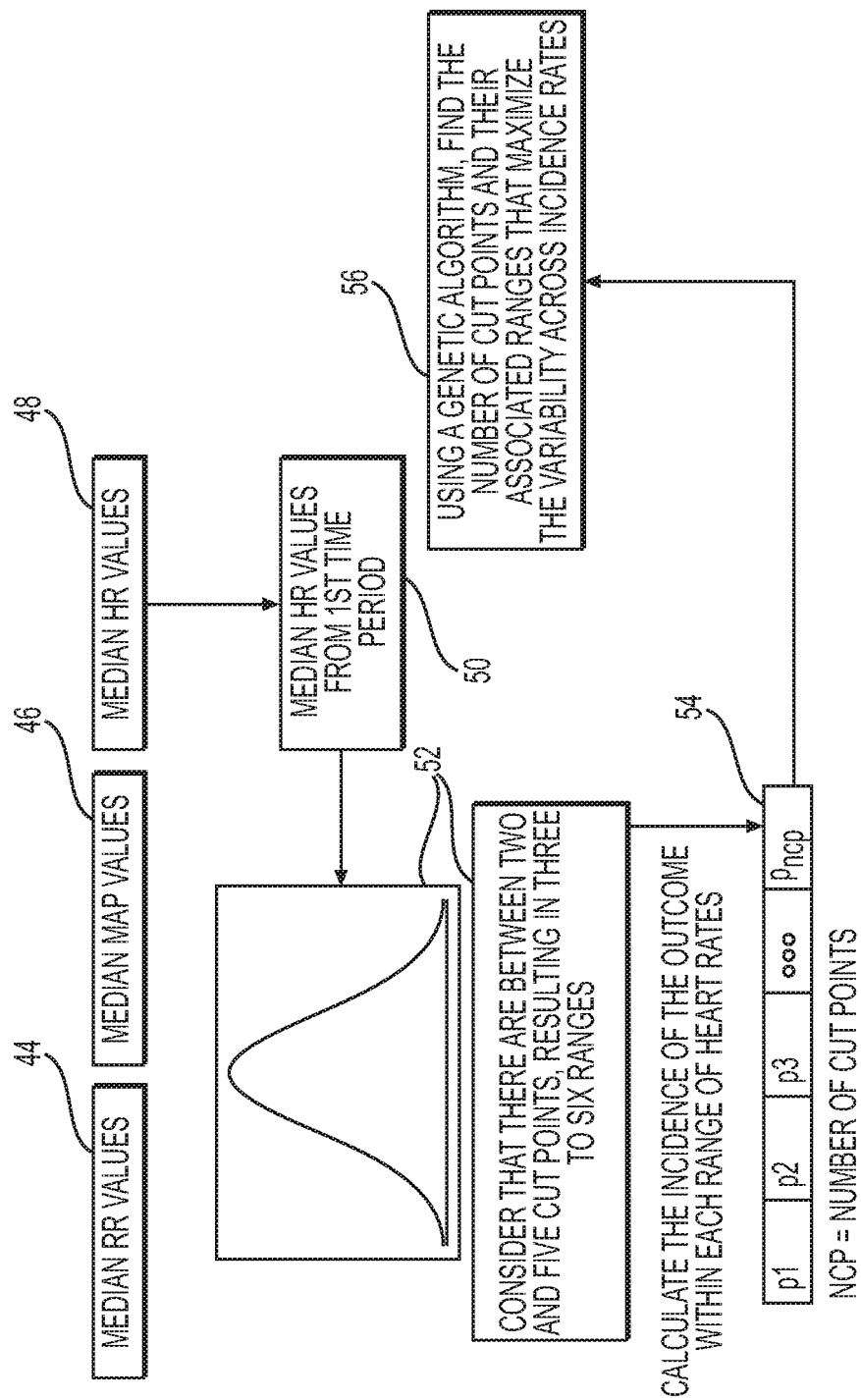
FIG. 3 is an explanation of determining the cut-points for a physiological vital sign.
Figure 4:
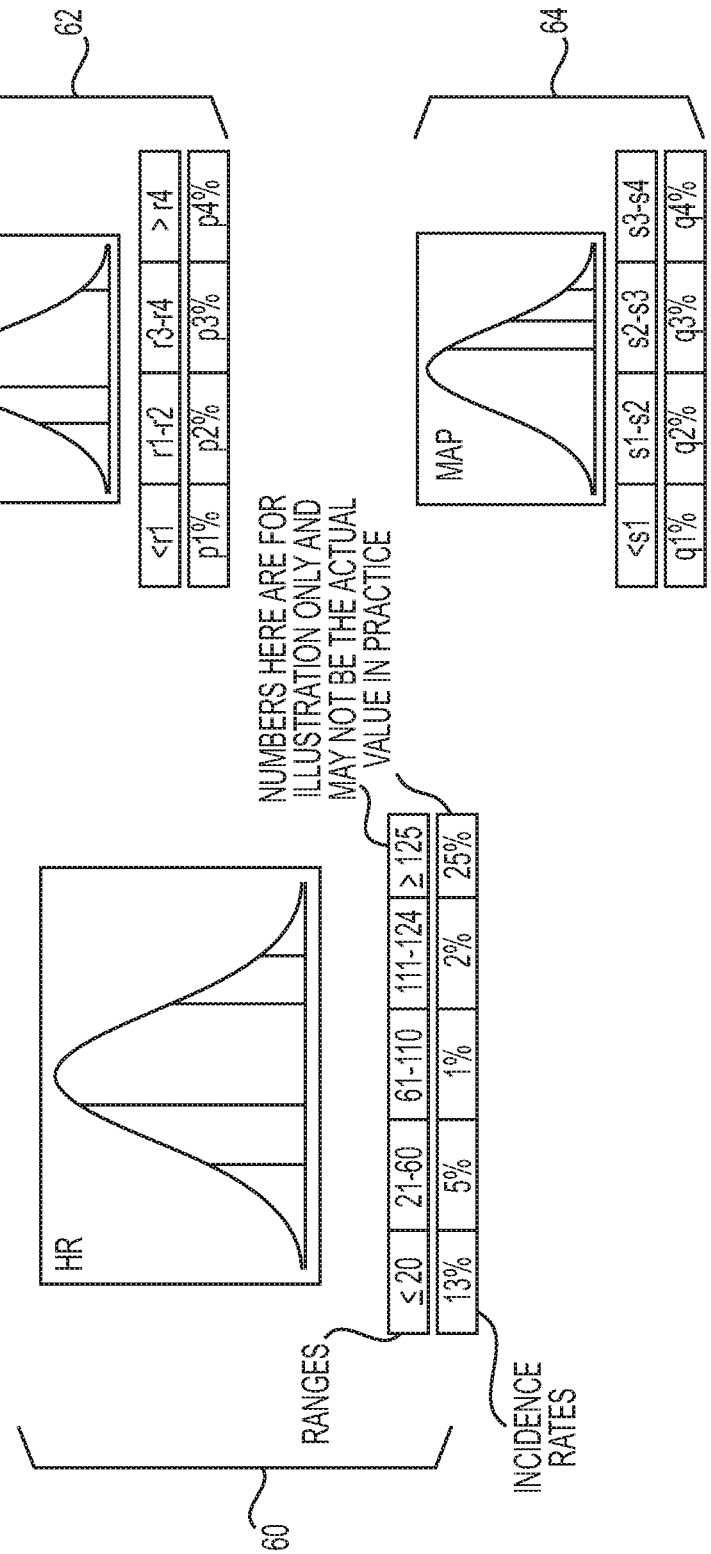
FIG. 4 is an explanation of discovery of the cut-points for each physiological vital sign.

Next, the median values of three example vital signs RR (respiratory rate) 44, MAP (mean arterial blood pressure) 46, and HR (heart rate) 48 are shown in FIG. 3. A time segment is determined a priori and can be from five to 30 minutes in length. A graph 52 shows a theoretical distribution for a vital sign. From this distribution, cut points and their respective ranges are determined based on the incidence of outcome for each. The median values during the first time segment are used to determine the cut-points 54 for each vital sign, resulting in bins of values (FIG. 3). This is accomplished by identifying the cut-points that maximize mortality rates across bins for each vital sign. FIG. 4 shows a hypothetical rendering of cut-points 60 for the example of heart rate and the resultant bins of values corresponding to them. The cut points are also demonstrated for respiratory rate 62 and mean arterial pressure 64. It should be noted that a patient might have differing numbers of cut-points across physiologic measures.

In the STUDY, every value of heart rate, respiratory rate, and mean arterial pressure, respectively, taken within the first 30 minutes after admission to the ICU were collected from the development data set. Personal median values for each vital sign for each patient were then obtained. A genetic algorithm was used to find the bins that optimized variability in mortality. Genetic algorithms are a heavily utilized tool for optimizing a set of outcomes given a complex mix of predictors. They do not make any assumption about the data's underlying distribution, making them superior to linear models for many types of biomedical analyses. The results from the STUDY are shown in Table 3.

TABLE 3

Cut-points that maximized the variability in mortality and the resultant bins

| Heart Rate | | Respiratory Rate | | Mean Arterial Pressure | |
|---|---|---|---|---|---|
| Cut-points | Bins | Cut-points | Bins | Cut-points | Bins |
| 62 | 5-62 | 13 | 4-13 | 65 | 40-65 |
| 72 | 63-72 | 19 | 14-19 | 72 | 66-72 |
| 98 | 73-98 | 28 | 20-28 | 93 | 73-93 |
| 111 | 99-111 | | >28 | 105 | 94-105 |
| | >111 | | | | >105 |

There were four cut-points apiece for heart rate and mean arterial pressure, resulting in five bins of measurements. Respiratory rate had three cut-points and therefore four bins. This illustrates that the number of bins is not fixed at a certain number, but instead are determined by the genetic algorithm's assessment of the data for discovering the maximum mortality variability.

Step Two: Assigning "Letters"

Figure 5:
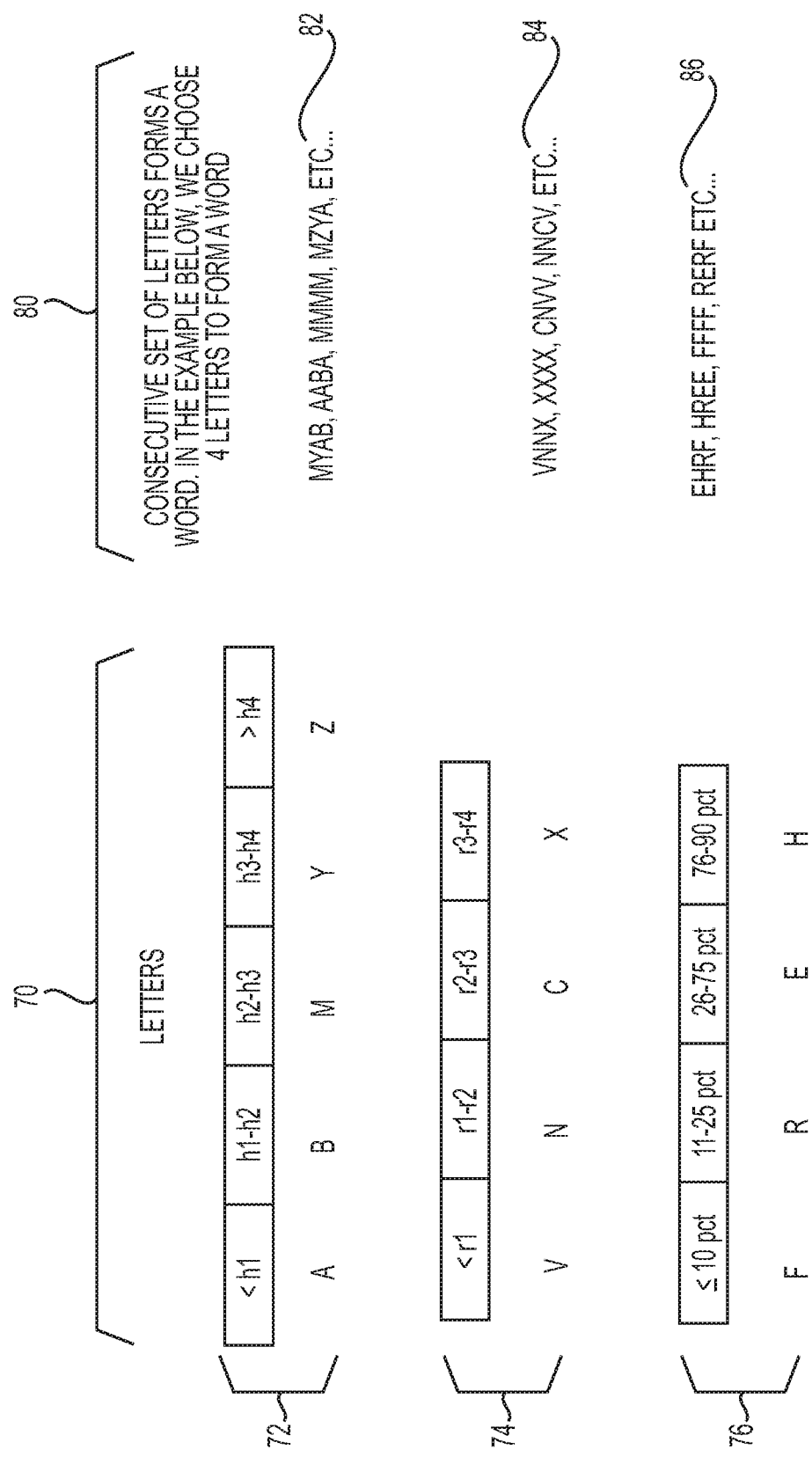
FIG. 5 is a demonstration of an example of assignment of letters and creation of words.

After the cut-points and resultant bins have been determined, the next step assigns letters to each vital sign (FIG. 5). In FIG. 5, three different physiological measures 70 are shown with arbitrary letters assigned to various bins of information. For physiological measurement 72, there are four cut points and five bins shown. Measurements 74 and 76 each have three cut points and four bins. It does not matter which letters (or any other symbols) are used in this step, just that the letters assigned to each bin for a vital sign are unique. That is, the same symbol cannot be used more than once for a specific vital sign's letters. This letter assignment is applied to the rest of a patient's time segments.

In the "STUDY", heart rate had five bins, and thus five letters were needed. Respiratory rate had four bins, while mean arterial pressure had four bins. The allocation of letters to each median vital sign corresponding to a 30 minute time segment is given in Table 4.

TABLE 4

Letters for each vital sign based on the results from Step One.

| Heart Rate | | Respiratory Rate | | Mean Arterial Pressure | |
|---|---|---|---|---|---|
| Bins | Letter | Bins | Letters | Bins | Letters |
| 5-62 | Q | 4-13 | R | 40-65 | E |
| 63-72 | Y | 14-19 | D | 66-72 | Y |
| 73-98 | M | 20-28 | F | 73-93 | K |
| 99-111 | B | >28 | A | 94-105 | C |
| >111 | J | | | >105 | B |

Step Three: Forming "Words"

After assignment of letters, words are formed by concatenating the letters from consecutive time segments for a pre-determined time period (FIG. 5). In FIG. 5, the identification of words 80 is shown by hypothetical example in three physiological measures 82, 84 and 86. The letters in these words 80 correspond to the example letters 70. In the "STUDY" two hours was a priori selected as the duration of time to form a word, i.e. time period. The reason for selecting two hours is that it may be the longest amount of time a clinician would want to wait for a potential alert to be generated. (In the situation where bedside monitors are consistently yielding data points, then alternatively a much smaller time segment is possible and indeed desirable.) So the same mapping of physiology to letters that was done for the first 30 minutes was continually applied to additional 30-minte time segments for the next 3.5 hours. The result was that all patients had eight letters for each of the three vital signs. Since a word was developed over each two hours, patients had two words for each vital sign. While this example illustrates 30-minute time segments, the time segment may alternatively be a predetermined time ranging from about 5 minutes up to 30 minutes, or further alternatively about 2 to 60 minutes. Table 5 shows one theoretical patient and how his/her measurements were mapped to words.

TABLE 5

Example showing how words were formed from the vital signs measurements for one patient: medians for each vital sign every 30 minutes

| | Letters | Words |
|---|---|---|
| Heart Rate | | |
| 64, 64, 112, 100, 121, 97, 96, 98 | Y, Y, J, B, J, M, M, M | YYJB, JMMM |
| Respiratory Rate | | |
| 29, 30, 34, 35, 29, 27, 26, 21, | R, R, R, R, R, D, D, F | RRRR, RDDF |
| Mean Arterial Pressure | | |
| 64, 63, 68, 69, 72, 72, 73, 70 | E, E, Y, Y, Y, Y, K, Y | EEYY, YYKY |

The patient in Table 5 had heart rate words of YYJB and JMMM; respiratory rate words of RRRR and RDDF; and mean arterial pressure words of EEYY and YYKY. This word formation was carried out for every patient.

Step Four: Identifying High-Risk Words and Patients

This step comprises taking the derived set of words and determining which ones are indicators of poor or negative clinical outcome. First, the frequency of each word is calculated, and then words with a frequency below a certain amount (say, 200 patients) are combined into the word "LLLL". These words occur too infrequently to be of any meaningful value by themselves.

Based on traditional statistical methods, at least 10 outcomes on average should be in every category. In the "STUDY", the overall mortality rate in the development data set was 6.2%. Thus 200 patients would yield approximately 12 fatalities for each word, and it was chosen as the minimum frequency for a word to stand alone rather than be aggregated with other low frequency words.

Figure 6:
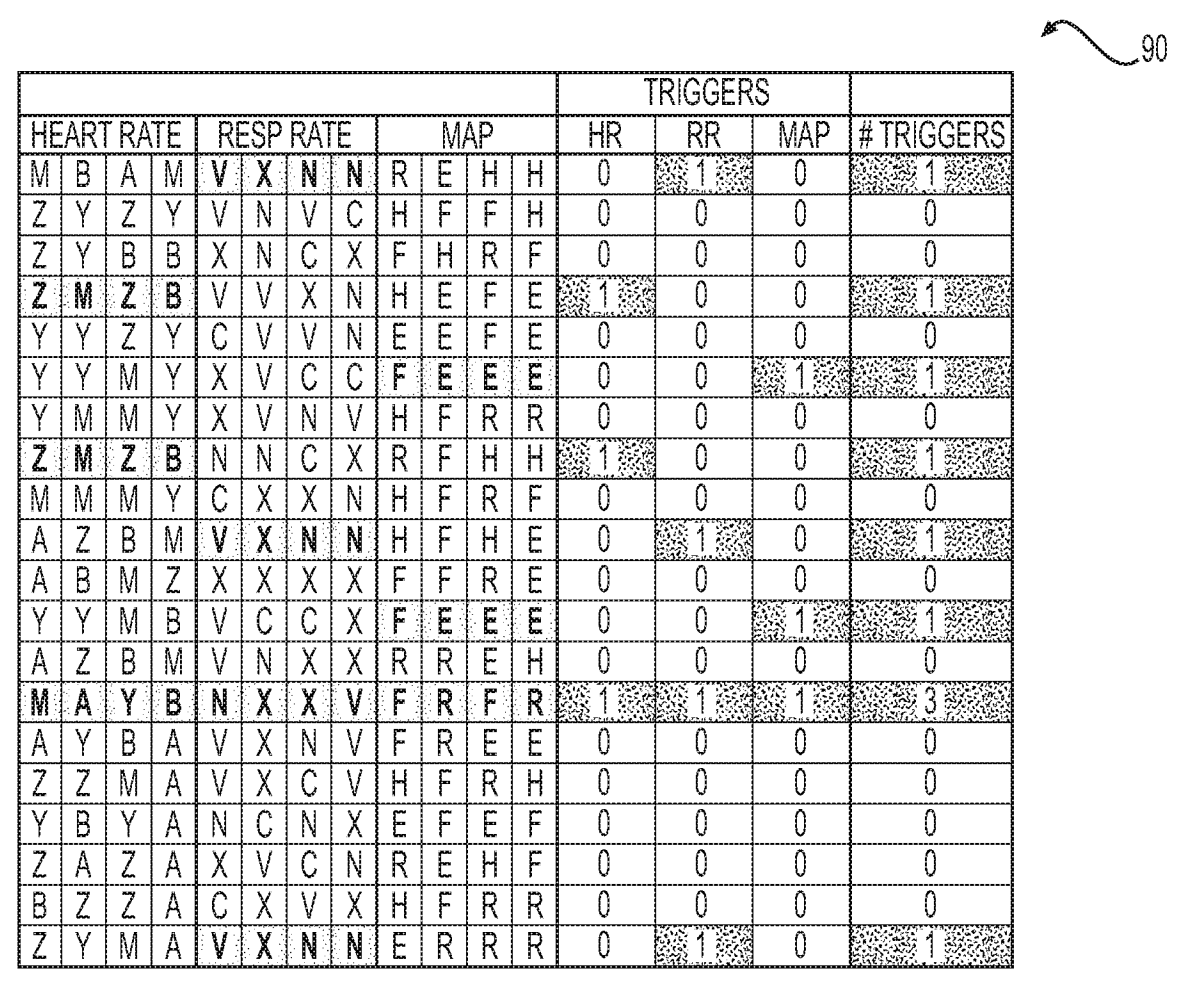

FIG. 6 illustrates a table 90 that describes where triggers are found in a hypothetical set of patients. Each word is initially given a random value of either zero or one. A value of one denotes that a word would prompt a "trigger" and zero means no trigger would be set. These triggers are shown as shaded on the left side of the table 90. If no triggers are set, the words are shown with a white background. Since each vital sign could be a trigger, a patient therefore might have {0, 1, 2, or 3} triggers. In the table in FIG. 6 only one word per vital sign is actually shown, but in practice there will be two words per vital sign. If both words for a vital sign prompt a trigger, this is only counted as one trigger (FIG. 6). Thus the total number of triggers is equal to the number of vital signs with triggers. Each patient is denoted as a pair of values: the number of triggers {0, 1, 2, or 3} and mortality (0=no, 1=yes).

Figure 7:
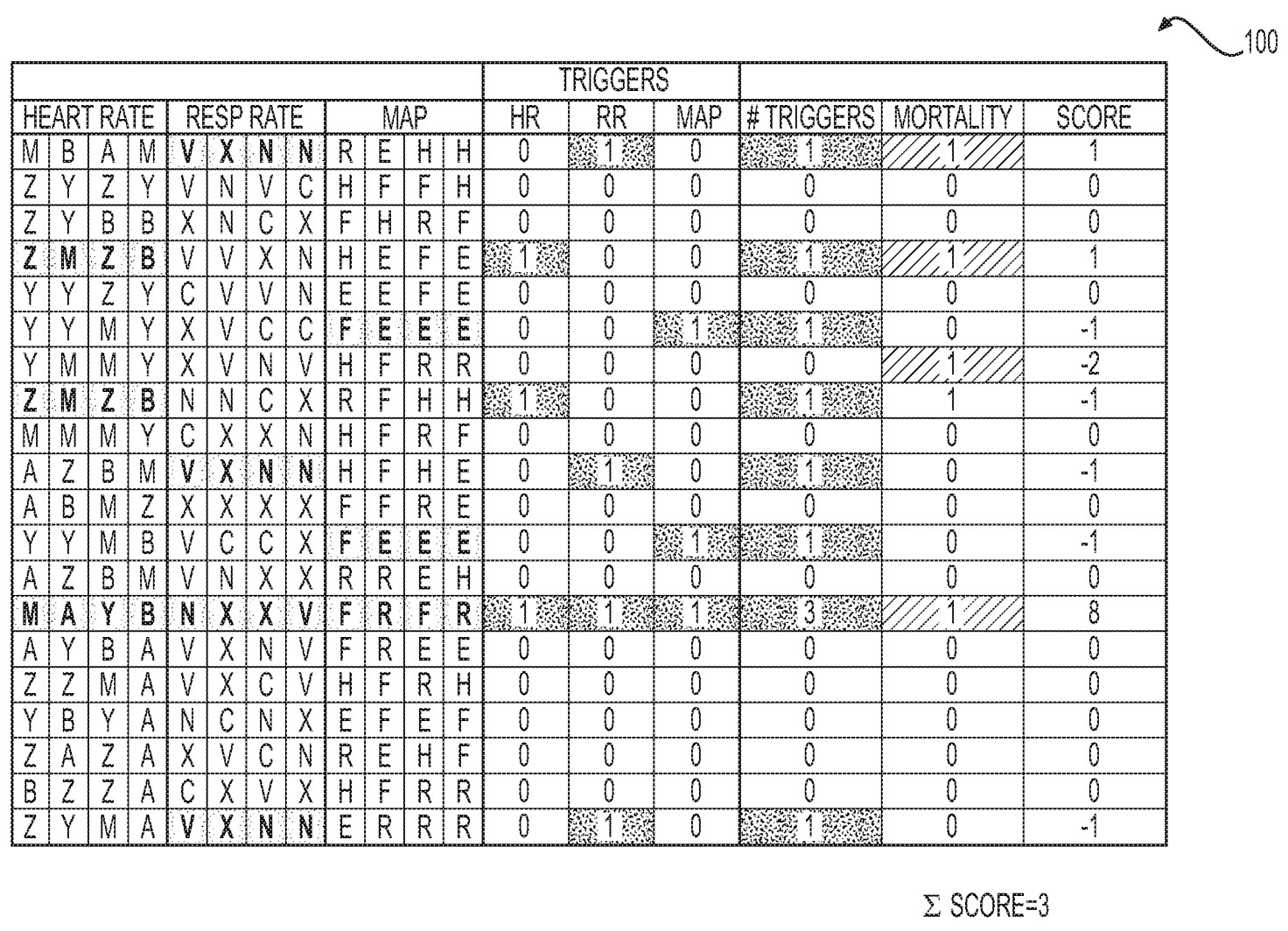

Since false negatives (no alerts but the patient died) are worse than false positives (an alert but no mortality), the specific pair of number of triggers along with outcome was given a "score" such that false negatives were more heavily punished than false positives (Table 6). These scores were derived from an earlier pilot study. The objective is to minimize the sum of scores over all patients, see table 100 in FIG. 7. As in FIG. 6, the triggers found in FIG. 7 are shaded on the left side of table 100.

TABLE 6

Scores assigned to each combination of number of triggers and mortality

| Number of Triggers | Mortality (0 = NO, 1 = YES) | Score |
|---|---|---|
| 0 | 0 | 0 |
| 0 | 1 | -2 |
| 1 | 0 | -1 |
| 1 | 1 | 1 |
| 2 | 0 | -1 |
| 2 | 1 | 4 |
| 3 | 0 | -1 |
| 3 | 1 | 6 |

Using a genetic algorithm, the initial value of zero or one given to each word is either flipped or remains the same in order to maximize the sum of scores over all patients. Once the sum of scores is maximized the words with a value equal to one are considered triggers. i.e. they increase the risk of mortality. The results of the genetic algorithm maximization for the "STUDY" using just the development data set are shown in Tables 7 and 8. There were a total of 13 words that were associated with an increased risk of mortality: four heart rate words, five respiratory rate words, and four mean arterial pressure words. Mortality increased from 4.8% for patients with no triggers to 37.5% for patients with three triggers. This is a 7.9-fold increased risk for the latter group. As the number of triggers increased from 0 to three the mortality rate correspondingly increased.

TABLE 7

Words that maximized the sum of scores for mortality

| Triggers | Words |
|---|---|
| Heart Rate | JJJJ, JJJB, BBBB, MMMB |
| Respiratory Rate | AAAA, AAAF, FFFF, DFFF, FAFA |
| Mean Arterial Pressure | KKYK, KYKK, EEEY, EEEE |

TABLE 8

Mortality rate by number of triggers: development data set

| Number of triggers | Mortality Rate | Increased Risk |
|---|---|---|
| 0 | 4.8% | Reference Group |
| 1 | 12.3% | 2.6 |
| 2 | 23.5% | 4.9 |
| 3 | 37.5% | 7.9 |

A good test of a predictive process is how well it performs on data that were not used in its development. Consequently the 13 triggers were applied to patients in the validation data set, and the results are given in Table 9.

TABLE 9

Mortality rate by number of triggers: validation data set

| Number of triggers | Mortality Rate | Increased Risk |
|---|---|---|
| 0 | 6.7% | Reference Group |
| 1 | 14.7% | 2.2 |
| 2 | 26.3% | 3.9 |
| 3 | 38.9% | 5.8 |

The results in the validation data set closely matched those obtained in the development data set. Mortality steadily increased from a low point for patients with no triggers to the highest rate in patients with three triggers. The mortality rates themselves were very similar to the corresponding rates in the development data set.

Step Five: Computer Code for Denoting which Words are Triggers

It is necessary to generate computer code that identifies which vital sign words elicit a trigger. The code can either be in Python, JAVA, C#, or SAS (or other applicable or compatible language); it is dependent on a hospital system's EMR. Per the steps described above, the computer code calculates the median value for each time segment; assigns a letter based on that value via a look-up table; concatenates letters to form a word; matches the words versus the set of triggers previously identified.

In the "STUDY" both SAS and Python were used. The personal median value for each vital sign for every patient was calculated for a 30-minute time segment; a total of eight consecutive segments. A letter was assigned to a personal median based on the values shown in Table 4 above. Two words were each formed by concatenating the letters from four contiguous time periods. Since patients had data collected for their first four hours after admission to the ICU, they had two words for each of the vital signs. These words were then mapped against the trigger-generating words shown in Table 7 above.

Step Six: Embedding Triggers into an EMR System and Generating Clinical Alerts

Figure 8:
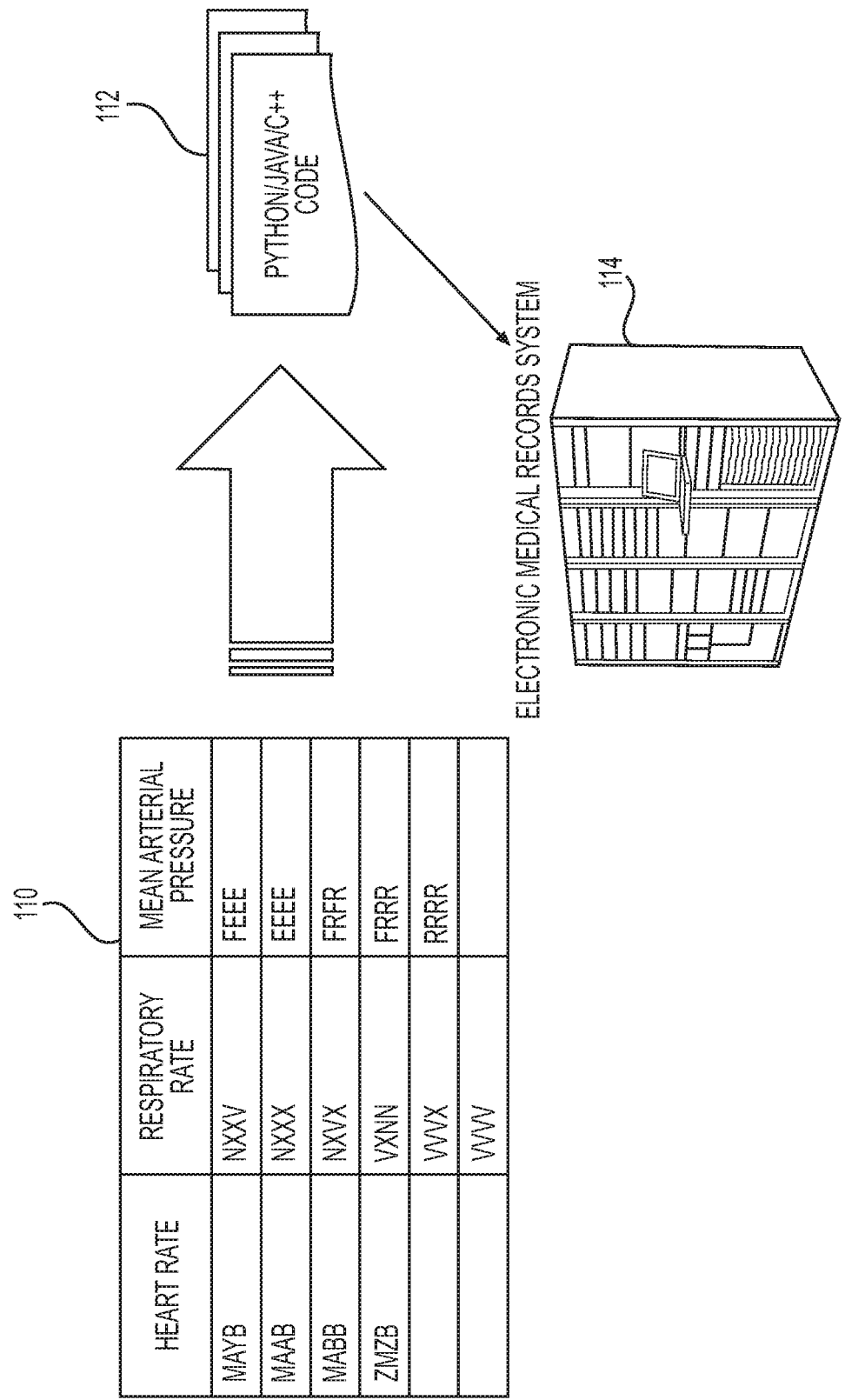
FIG. 8 is an example of words that may then be embedded in a hospital EMR system.
Figure 9:
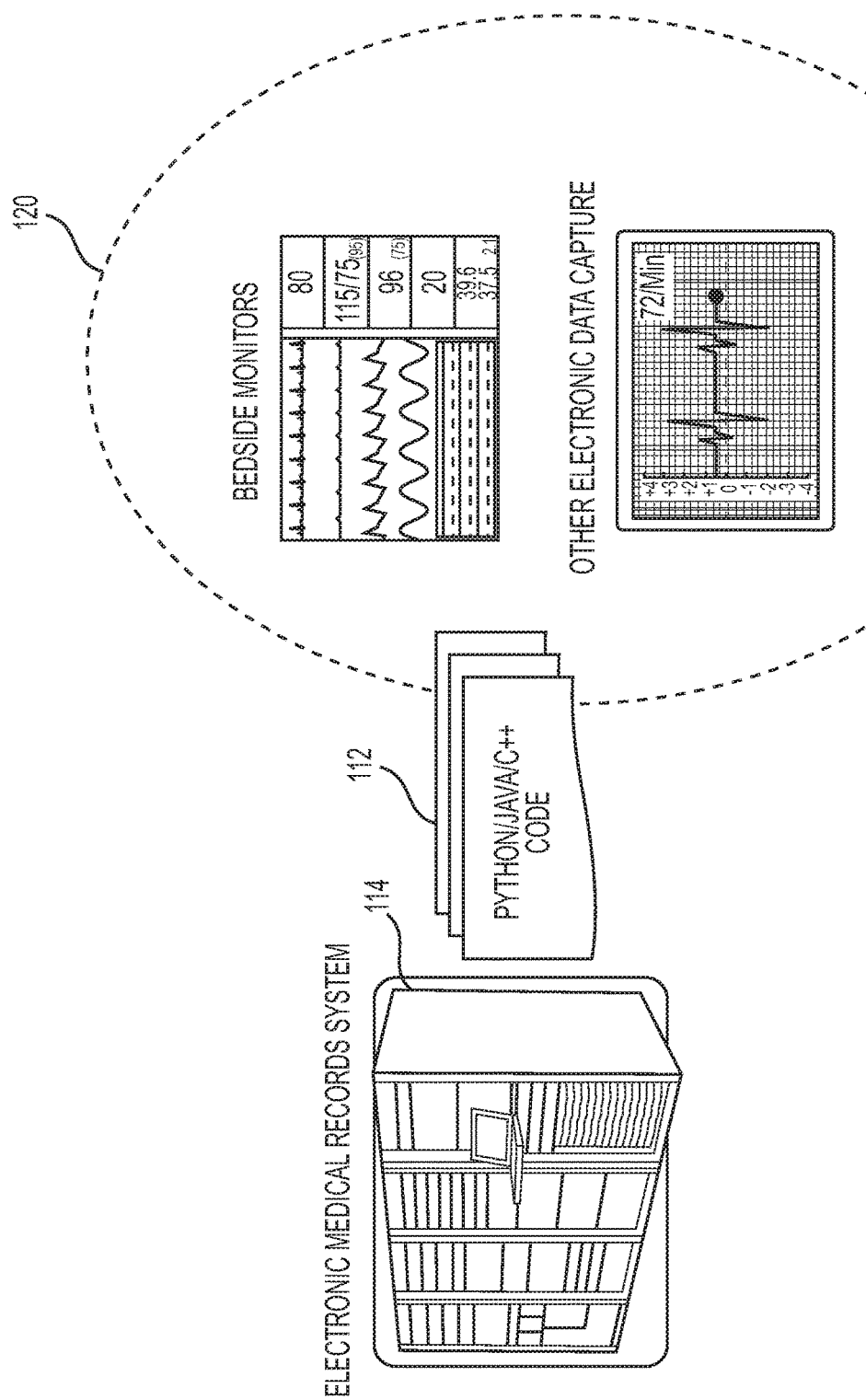
FIG. 9 is a schematic of data that are collected and matched against trigger words.

In FIG. 8, the trigger-generating words 110 are then processed in the computer code 112 for Step Five and then embedded into a hospital's EMR system 114 (FIG. 8). It sits on top of the EMR and continually pulls time-stamped vital signs data 120 on each patient admitted to an ICU into a database (FIG. 9). The amount of embedded code for this part is not extensive, as the all of the analyses for identifying trigger words have been previously carried out.

In the "STUDY", computer code that identifies the triggers shown in Table 5 has been generated and is going to be embedded into Medical Decision Network's next release of their Phoenix ICU database solution. Once a patient has been admitted to an ICU and "enrolled" into Phoenix, data are electronically captured via HL-7 feeds. These data values are passed to the present system, which then assesses them as described in Step Five above.

Step Seven: Generating Clinical Alerts Based on the Number of Triggers

Figure 10:
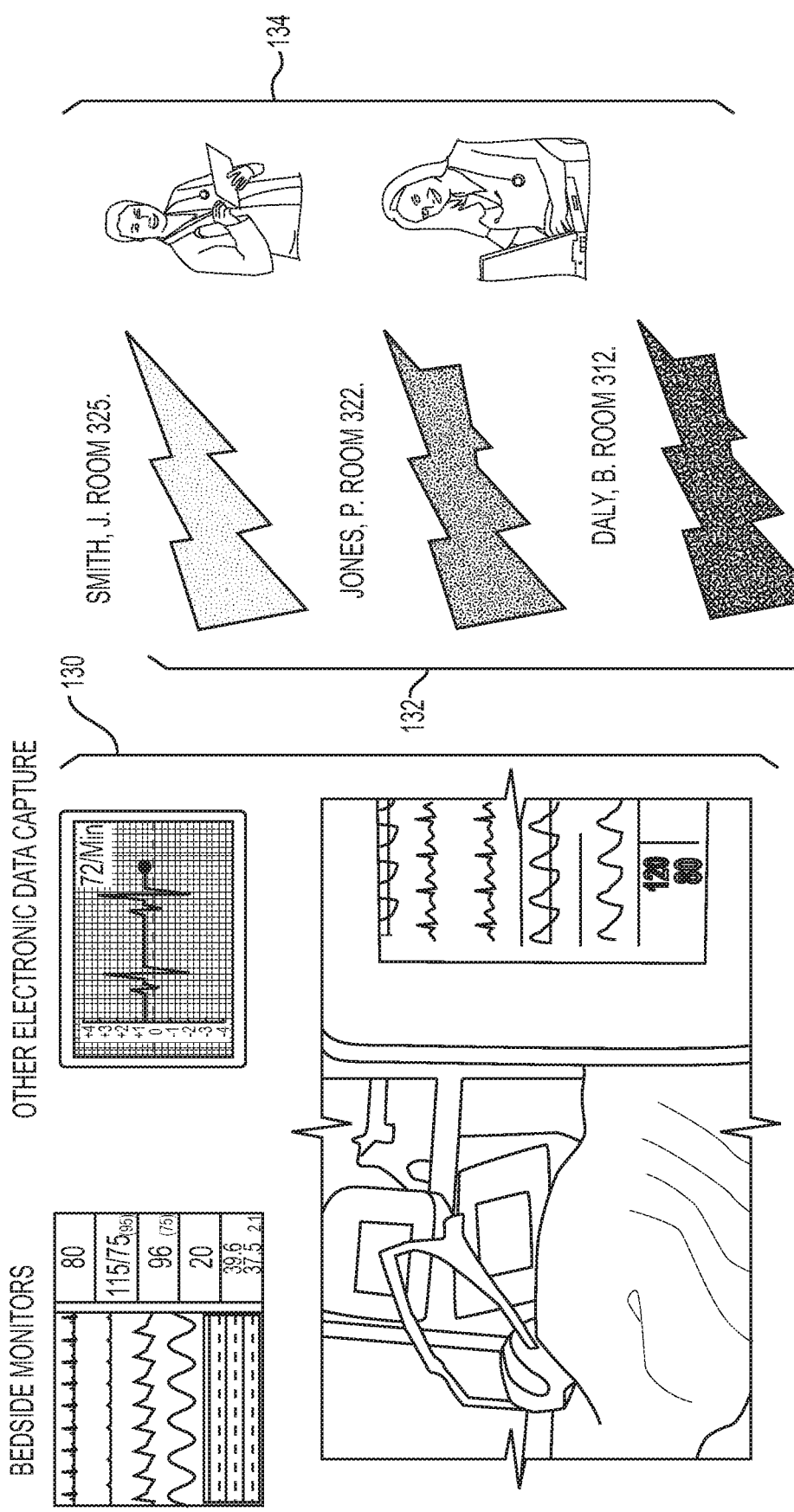
FIG. 10 illustrates that the number of triggers regarding a specific patient determines the kind/level of alert that is sent.

A patient receives their first word after the initial time period has elapsed. If during this time a patient has any of the informative words, then that patient is identified as vulnerable. Based on the patient physiological data 130, the present system code sends a signal 132 to the medical personnel 134 caring for that patient (FIG. 10). Exemplary signals 132 are shown in a color-coded scheme in FIG. 10. For patients with one trigger, an icon with the following information is sent: patient's name, room number, and a yellow flag indicating that the patient has one trigger. This signal is an alert that this patient is at an elevated mortality risk, and should be monitored carefully. Patients with two triggers have the same information forwarded except that they have a red flag in their icon. These patients have a high risk of mortality, and should be attended to. Finally, patients with three triggers have a scarlet flag in their icon that flashes every second to alert the physician that the patient is at a very high risk of expiring without remedial treatment. After another time period has elapsed, patients' words are identified for any additional triggers. Thus the number of vital signs with a trigger is cumulative, starting with the first time period and succeeding through the last period.

In the "STUDY", the first time period is two hours. Thus after two hours if a patient has one trigger a yellow warning signal is sent for that patient; two triggers evoke a red alert signal; and three triggers generate a flashing scarlet alert. After another two hours each patient's second word for every vital sign is checked. If a vital sign that previously did not generate a trigger has such a word in the second time period, a trigger is now generated for that vital sign. Since the observation period was set at four hours, two time periods is the duration of time for generating triggers. It should be noted that the cumulative nature of generating triggers means that a patient's status can never recede. If a patient's condition escalates during the second time period, then that piece of information is vitally important to the attending clinicians. This makes sense clinically, as once a patient has a trigger, they are vulnerable for the duration of their time in the ICU.

Figure 11:
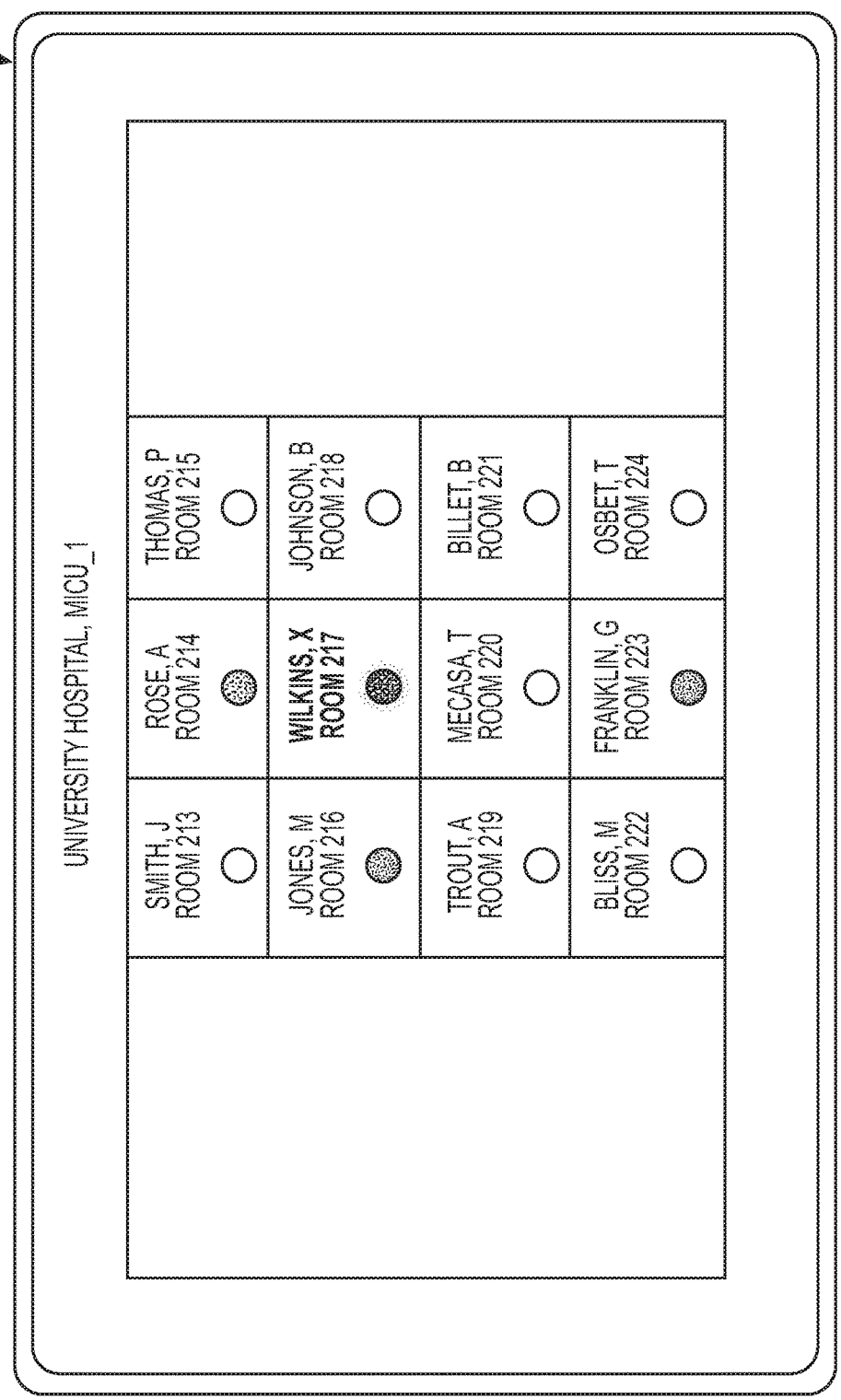
FIG. 11 is an example of a unit view of multiple patients and their risk level.

In addition to alerts being sent out, the system also populates an ICU's unit view 140 of their patients (FIG. 11). The icon (different-colored circle) for every patient in the unit is placed in a single screen so that clinical staff in that ICU get an overall view of the severity level of their patients. For patients who remain "non-vulnerable" (i.e. do not have a trigger generated-white circle) it does not mean that these patients are at no risk of mortality. It just means that their risk is considerably lower than vulnerable patients.

It should be noted that the words that generate triggers which are shown in Table 7 are applicable to patients in the hospitals participating in the "STUDY". While these words might also be triggers at other hospitals, the steps described above should be repeated for any new hospital organization in which the system and method are being employed.

Collecting data, interpreting it, and sending alerts for mortality before discharge from the ICU is not the only use case for the present system and method. This method and system described herein could be utilized for virtually any outcome, and two such additional use cases shown below are demonstration of that.

Additional Use Case #1: Identifying Patients Who have an Increased Risk of being Placed on Mechanical Ventilation About 15-25% of all patients admitted to an ICU require invasive mechanical ventilation (MV) sometime within the first six hours of their stay. (This does not include BIPAP or CPAP, which are non-invasive methods of supplementing room air.) A small but noticeable number of patients not intubated for the first six hours after admission to an ICU eventually need MV before discharge from the unit. These patients require substantial resources, and identifying these patients early during their time in the ICU might help to limit this escalation of the patient's treatment.

The analytic part of the present process was carried out for 39,983 admissions from Medical Decision Network's Phoenix ICU database. These patients had remained in the ICU for six hours and not received MV. The aim was to see if the system could identify patients at a high risk of subsequently needing MV. Methodology similar to the "STUDY" identified words that were significantly associated with the need for MV. Table 10 shows the results of the analysis when the triggers were applied to the validation data set. (There were very few patients with three triggers, so they were added to the group with two triggers.)

TABLE 10

Number of SIGNIPHY triggers versus subsequent need for mechanical ventilation (MV): Results from the validation data set

| Number of Triggers | % Requiring MV | Increased Risk |
| --- | --- | --- |
| 0 | 3.3% | Reference Group |
| 1 | 9.1% | 2.8 |
| 2-3 | 21.4% | 6.5 |

The results here are comparable to those obtained when mortality was the outcome. Patients with no triggers were at the lowest risk, those with one trigger had a modestly high risk, and patients with two or three triggers had the highest risk for needing MV. Patients in the highest risk group had a 6.5-fold increased chance of requiring MV during their time in the ICU.

The physiologic patterns (i.e. words) that serve as triggers will be embedded into Phoenix, and alerts sent to clinicians in the same manner as those for mortality. The benefit of applying this invention to other clinical outcomes will also be explored.

Additional Use Case #2: Identifying Patients with an Increased Risk of Expiring on a Unit of Lesser Acuity or being Sent to Hospice after being Discharged from the ICU.

Clinicians have to make many decisions while a patient is in the intensive care unit (ICU). Arguably the most difficult decision is whether a patient is ready for discharge to a unit of lesser acuity. If the patient discharge is unduly delayed, then a prolonged ICU stay with the attendant problems of cost and risk of infection is possible. Conversely, a patient discharged prematurely might be at high risk for mortality on the floor of the hospital.

Intensivists could benefit greatly when making a decision about a patient's ICU discharge by having a tool available that identifies patients at high risk for either subsequent mortality on the hospital floor or being placed in hospice. The present system was utilized to eventually make this tool available for hospitals' EMR systems. A cohort of 32,085 patients discharged alive from the ICU were identified. Using vital signs data transmitted from three hours before discharge to one hour before discharge, the system found 15 words that were associated with an increased risk of mortality on the hospital floor or discharge to a hospice. When applied to the validation data set, the results (shown in Table 11) were impressive, and corresponded to the results obtained from other Use Case of the system.

TABLE 11

Rate of mortality or discharge to a hospice for patients discharged alive from the ICU: rate by number of triggers, by number of system triggers

| Number of triggers | Mortality or Hospice | Increased Risk |
| --- | --- | --- |
| 0 | 3.2% | Reference Group |
| 1 | 7.5% | 2.4 |
| 2 | 13.3% | 4.2 |
| 3 | 27.5% | 8.7 |

The system makes it possible to use vital signs proximate to when a discharge decision is made to identify patients with an increased risk of either mortality or discharge to hospice after leaving the ICU.

SUMMARY

The results from all of the studies that utilized the system are given in Table 12. There are two additional studies included in that table: detection of high-risk patients in a huge public ICU database made available by Phillips Corporation and an application across all-levels of care in an acute care North American hospital. In all, a total of five situations in which this system was utilized are listed. What is extraordinary is how consistent the results are across studies that used different populations and different outcomes.

Clearly, the system is uncovering heretofore unknown physiologic patterns that proceed patient deterioration. The second part of the method and system, that is, the sending of alerts to clinicians based on alert words that were identified, is of utmost importance.

TABLE 12

Summary of results for trigger identification using the system

| Population | MDN* | Phillips** | MDN | North Am Hospital*** | MDN, discharged alive from ICU |
| --- | --- | --- | --- | --- | --- |
| Outcome | Mortality | Mortality | Need for MV | Mortality | Mortality or Hospice |
| Increased Risk* | Increased Risk† | Increased Risk† | Increased Risk† | Increased Risk† | Increased Risk† |
| One Trigger | 2.2-fold | 2.2 | 2.8 | 3.7 | 2.4 |
| Two Triggers | 3.9-fold | 4.1 | 6.6 | 7.1 | 4.2 |
| Three Triggers | 5.8-fold | 6.6 | N/A | 14.5 | 8.7 |

*MDN = Medical Decision Network's ICU database
**Philips = Philips, Inc.'s ICU database
***North Am Hospital = All patients admitted to a North American hospital that wishes to remain anonymous
† = The increased risk over a patient having no triggers, e.g. a 2.2-fold risk means a patients with one trigger had a 2-2-fold increased chance of developing the outcome (usually mortality).

Other embodiments of the present invention will be apparent to those skilled in the art from consideration of the specification. It is intended that the specification and figures be considered as exemplary only, with a true scope and spirit of the invention being indicated by the claims.

That which is claimed is:

1. A method for identifying and managing high-risk patients comprising the steps of:
providing a clinical setting for a first patient wherein the setting includes a plurality of physiological monitors;
providing electronic devices to a caregiver in the clinical setting;
providing a first database that stores historical physiological measurements of a plurality of former patient physiological measurements and former patient outcomes of those former patients; and for each historical physiological measurement, dividing up the historical physiological measurements into ranges to form bins, calculating a distribution of 3-6 bins that results in a maximum variability in a historical mortality outcome rate, and assigning a different letter to each bin;
defining first database trigger measurements based on the historical physiological measurements, wherein those trigger measurements represent a set of historical physiological measurements that have been identified as indicating a high risk for a negative clinical outcome;
providing a second database that receives and stores a plurality of measurements from the plurality of the first patient physiological monitors wherein the first patient physiological measurements occur at regular time segments; and
wherein a bin letter is assigned for each time segment for each first patient physiological measurement depending on which bin the first patient physiological measurement is in;
saving the bin letters assigned for each first patient physiological measurement and for each historical physiological measurement, and collecting the letters for a predetermined time period which is comprised of a plurality of time segments;
forming a word with the plurality of bin letters associated with each time period, and identifying a trigger word that corresponds to a trigger measurement and that indicates an increase in a chance of a negative clinical outcome;

wherein the historical physiological measurements and first patient physiological measurements are recorded and saved for each of a predetermined time segment of 5 to 30 minutes, and for each predetermined time segment, the historical physiological measurement and the first patient physiological measurements are median values of all data points for a physiological measure for a single individual during the predetermined time segment;

providing a processor and comparing by the processor the first patient physiological measurement words to the trigger words to identify a high-risk patient based on whether the first patient set of physiological measurements correspond to the first database trigger measurements; and sending by the processor an alert to the caregiver if the first patient is at a high risk for a negative outcome based on the comparing step.

2. A method for identifying and managing high-risk patients as described in claim 1,
wherein the historical physiological measurements and first patient physiological measurements are selected from a group consisting of heart rate, respiratory rate, mean arterial pressure, saturated oxygen, temperature, glucose level, platelet count and white blood cell count.

3. A method for identifying and managing high-risk patients as described in claim 1,
wherein the alert sent to the caregiver comprises visual indicia sent to a user interface on the caregiver electronic device with respect to the first patient.

4. A method for identifying and managing high-risk patients as described in claim 1,
wherein the alert sent to the caregiver comprises a visual and audible sound sent to the caregiver electronic device with respect to the first patient.

5. A method for identifying and managing high-risk patients as described in claim 1,
wherein the word has four letters which represent historical and first patient physiological measurements, one for each segment, for four time segments.

6. A system for identifying and managing high-risk patients comprising:
a clinical setting for a first patient wherein the setting includes a plurality of physiological monitors;
electronic devices for a caregiver in the clinical setting;
a first database that stores historical physiological measurements in the clinical setting of a plurality of former patient physiological measurements and former patient outcomes of those former patients; and for each historical physiological measurement, dividing up the historical physiological measurements into 3-6 ranges to form bins, wherein a distribution of bins results in a maximum variability in a historical mortality outcome rate, and assigning a different letter to each bin;
in the first database, a set of trigger measurements based on the historical physiological measurements, wherein those trigger measurements represent a set of historical physiological measurements that have been identified as indicating a high risk for a negative clinical outcome;
a second database that receives and stores a plurality of measurements from the plurality of the first patient physiological monitors wherein the first patient physiological measurements occur at regular time segments;
wherein in the second database a bin letter is assigned for each time segment for each first patient physiological measurement depending on which bin the first patient physiological measurement is in,
saving the bin letters assigned for each first patient physiological measurement and for each historical physiological measurement, and collecting the letters for a predetermined time period which is comprised of a plurality of time segments;
forming a word with the plurality of bin letters associated with each time period, and identifying a trigger word that corresponds to a trigger measurement and that indicates an increase in a chance of a negative patient outcome;
wherein the historical physiological measurements and first patient physiological measurements are recorded and saved for each of a predetermined time segment of 5 to 30 minutes, and for each predetermined time segment, the historical physiological measurement and the first patient physiological measurements are median values of all data points for a physiological measure for a single individual during the predetermined time segment;
a processor for comparing the first patient physiological measurement words to the trigger words to identify a high-risk patient based on whether the first patient set of physiological measurements correspond to the first database trigger measurements; and
an alert sent by the processor to the caregiver if the first patient is at a high risk for a negative outcome based on the comparing step.

7. A system for identifying and managing high-risk patients as set forth in claim 6,
wherein the alert sent to the caregiver comprises visual indicia sent to a user interface on the caregiver electronic device with respect to the first patient.

* * * * *